US009580734B2

(12) United States Patent
Shankar et al.

(10) Patent No.: US 9,580,734 B2
(45) Date of Patent: Feb. 28, 2017

(54) PRODUCTION OF HIGH YIELDS OF BACTERIAL POLYSACCHARIDES

(71) Applicant: Serum Institute of India Ltd., Pune (IN)

(72) Inventors: Pisal Sambhaji Shankar, Pune (IN); Chilukuri Srinivas Reddy, Pune (IN); Peddireddy Srinivas Reddy, Pune (IN)

(73) Assignee: Serum Institute of India Private Ltd., Pune (IN)

( * ) Notice: Subject to any disclaimer, the term of this patent is extended or adjusted under 35 U.S.C. 154(b) by 0 days.

(21) Appl. No.: 14/646,089

(22) PCT Filed: Nov. 18, 2013

(86) PCT No.: PCT/IN2013/000701
§ 371 (c)(1),
(2) Date: May 20, 2015

(87) PCT Pub. No.: WO2014/080423
PCT Pub. Date: May 30, 2014

(65) Prior Publication Data

US 2015/0299750 A1 Oct. 22, 2015

(30) Foreign Application Priority Data

Nov. 21, 2012 (IN) ........................ 3337/MUM/2012

(51) Int. Cl.

| | |
|---|---|
| ***C12P 19/04*** | (2006.01) |
| ***A61K 39/095*** | (2006.01) |
| ***C08B 37/00*** | (2006.01) |
| ***C12P 19/26*** | (2006.01) |
| ***C12N 1/20*** | (2006.01) |
| ***C07K 14/22*** | (2006.01) |
| ***C07K 14/33*** | (2006.01) |

(52) U.S. Cl.
CPC ............ *C12P 19/04* (2013.01); *A61K 39/095* (2013.01); *C07K 14/22* (2013.01); *C07K 14/33* (2013.01); *C08B 37/0003* (2013.01); *C08B 37/0063* (2013.01); *C12N 1/20* (2013.01); *C12P 19/26* (2013.01)

(58) Field of Classification Search
None
See application file for complete search history.

(56) References Cited

U.S. PATENT DOCUMENTS

| | | | |
|---|---|---|---|
| 4,235,994 | A | 11/1980 | Stoudt et al. |
| 6,933,137 | B2 | 8/2005 | Egen et al. |
| 2010/0272755 | A1 | 10/2010 | Costantino et al. |

FOREIGN PATENT DOCUMENTS

| | | | |
|---|---|---|---|
| CA | 2766418 | A1 | 4/2011 |
| WO | 2007/084856 | A2 | 7/2007 |

OTHER PUBLICATIONS

Kenny et al., "A Chemicall Defined Protein-free Liquid Medium for the Cultivation of Some Species of Neisseria", Bull. World Health Organ, vol. 37, No. 4, 1967, pp. 569-573.
Bundle et al., "Studies on the Grou-specific Polysaccharide of Neisseria meningitidis Serogroup X and an Improved Procedure for Its Isolation", The Journal of Biological Chemistry, vol. 249, No. 15, Aug. 10, 1974, pp. 4797-4801.
International Search Report for PCT/IN13/00701, mailed on Jan. 23, 2015. 3 pages.

*Primary Examiner* — Oluwatosin Ogunbiyi
(74) *Attorney, Agent, or Firm* — Fish & Richardson P.C.

(57) ABSTRACT

The instant invention provides improved culture, fermentation and purification conditions for preparing *Neisseria meningitidis* polysaccharides. The invention in particular relates to a novel fermentation medium, optimal feed solution addition strategies and an improved purification process devoid of any chromatographic methods for obtaining high yield of *Neisseria meningitidis* X polysaccharide.

18 Claims, 4 Drawing Sheets

PRODUCTION OF HIGH YIELDS OF BACTERIAL POLYSACCHARIDES

TECHNICAL FIELD

The invention concerns vaccines against *Neisseria meningitidis*

BACKGROUND ART

*Neisseria meningitidis* is the cause of epidemic bacterial meningitis. Capsular polysaccharide is a major virulence determinant of *N. meningitidis*. Among the 13 meningococcal serogroups classified based on capsular polysaccharide structure, serogroups A, B, C, Y, and W135 are associated with the majority of cases of meningococcal disease. In the African meningitis belt most large epidemics have been caused by serogroup A meningococci, whereas sporadic disease and outbreaks in developed countries are usually caused by serogroup B and C meningococci. Serogroup Y meningococci emerged as an important cause of sporadic disease and outbreaks in the United States in the late 1990s, and in 2000 serogroup W135 meningococci caused worldwide disease in association with the Hajj pilgrimage and large outbreaks in sub-Saharan Africa.

Serogroup X *Neisseria meningitidis* (MenX), previously a rare cause of sporadic cases of meningitis, has recently been associated with increased incidence of meningococcal disease and has emerged as a cause of large outbreaks in the "Meningitis Belt" of Africa. Outbreaks have been documented in Niger, Burkina Faso, Togo and Ghana and have varied in size. In the meningitis season of 2010 over 6500 meningitis cases were reported in Burkina Faso, and it is reasonable to assume that at least 1000 of these cases were due to MenX with a locally reported incidence of 120 cases per 100,000. Earlier, several patients were confirmed with MenX disease in an outbreak of at least 82 cases of bacterial meningitis on the border of Kenya and Uganda in 2007.

The capsular polysaccharides of serogroup B, C, Y, and W135 meningococci are composed of sialic acid derivatives. Serogroup B and C meningococci express ($\alpha$2-8)- and ($\alpha$2-9)-linked polysialic acid, respectively, while alternating sequences of D-glucose or D-galactose and sialic acid are expressed by serogroup Y and W135 *N. meningitidis*. In contrast, the capsule of serogroup A meningococci is composed of ($\alpha$1-6)-linked N-acetylmannosamine 6-phosphate, while *N. meningitidis* serogroup X synthesizes capsular polymers of ($\alpha$1-4)-linked N-acetylglucosamine 1-phosphate.

The increase in incidence of MenX disease in African Meningitis Belt in the last 5 years warrants development and introduction of a MenX vaccine in selected areas of the region to prevent and control future epidemics. The conjugation of meningococcal capsular polysaccharides to a carrier protein has led to the development of monovalent (A or C) polysaccharide conjugate vaccines with high effectiveness, and immunogenicity data from clinical trials indicate that wide use of tetravalent conjugate vaccines covering serogroups A, C, Y and W-135 may be similarly effective. A similar approach may also be fruitful for MenX. Refer Ouli Xiea et al "Characterization of size, structure and purity of serogroup X *Neisseria meningitidis* polysaccharide, and development of an assay for quantification of human antibodies", Vaccine 30, 2012.

Gunnstein Norheim discusses that at present vaccine against serogroup X is not available and that next generation affordable vaccines should target most prevalent serogroups: A, W-135, X. Refer "Preventing the emerging serogroup X meningococcal disease in the African. Meningitis Belt" Oxford Vaccine Group, 2011.

The lack of a vaccine against group X meningococci is a cause for concern given the outbreaks caused by meningococci of this serogroup in the past few years. Refer "Meningococcal vaccines: WHO position paper", November 2011.

In order to facilitate Men X polysaccharide based conjugate vaccine development, it is necessary to obtain structurally intact Men X polysaccharides with higher yields.

Several synthetic media were discovered for large-scale production of meningococcal polysaccharide (Frantz, I. D. Jr. Growth Requirements of the Meningococcus. J. Bact., 43: 757-761, 1942; Catlin, B. W. Nutritional profiles of *Neisseria lactamica, gonorrhoeae* and *meningitidis*, in chemically defined media. J. Inf. Dis., 128(2): 178-194, 1973; Watson-Scherp Medium: Watson R G, et al. The specific hapten of group C (group IIa) meningococcus, II. Chemical nature. J Immunol 1958; 81:337-44; Marcelo Fossa da Paz; Júulia Baruque-Ramos; Haroldo Hiss; Márcio Alberto Vicentin; Maria Betania Batista Leal; Isaías Raw. Polysaccharide production in batch process of *Neisseria meningitidis* serogroup C comparing Frantz, modified Frantz and Catlin 6 cultivation media, Braz. J. Microbiol. vol. 34., no. 1. São Paulo January/April 2003).

U.S. Pat. No. 5,494,808 reports a large-scale, high-cell density (5 g/L dry cell weight, and an optical density of between about 10-13 at 600 nm) fermentation process for the cultivation of *N. meningitidis*(serogroup B 11). This patent disclose the following medium (called "MC.6") for culturing *Neisseria meningitidis* for isolation of OMPC ("Outer Membrane Protein Complex")

U.S. Pat. No. 7,399,615 discloses a fermentation composition wherein the composition omits $NH_4Cl$, and an improved method' of fermenting *Neisseria*(serogroups A, C, Y & W135) in a fermentation composition replaces ammonium chloride(nitrogen source) with a soy peptone(HSP-A; Nutricepts, Inc; Minneapolis, Minn.). The said fed batch fermentation(2 L), wherein the fermentation medium as well as feed solution contains HSP-A results in Men A polysaccharide yield of about 1300-1400 mg/l at an average max OD between 14-20.

U.S. Pat. No. 7,491,517 discloses a *Neisseria meningitidis* fastidious culture medium (NMFM) for producing capsular polysaccharides from *Neisseria meningitidis*(serogroups A, C, Y & W135) comprising: DI (deionizer) water, NaCl, $K_2SO_4$, KCl, trisodium citrate.$2H_2O$, $MgSO_4.7H_2O$, $MnSO_4.H_2O$, $MnCl_2.6H_2O$, vitamin. B12, NAD (Nicotinamide Adenine Dinucleotide) thiamine HCl, soy peptone, D-glucose, L-glutamic acid, L-arginine, L-serine, L-cysteine, glycine, morpholinepropanesulphonic acid [MOPS], $CaCO_3$ to maintain pH at 6.5 to 7.0 and $Fe_2(SO_4)_3$ for serogroup A and $NH_4Cl$ for serogroup W-135. The said fermentation results in polysaccharide yield of about 30-40 mg/L at an average max OD of 10.

David Bundle et al discusses preparation and isolation of Men X polysaccharide from *N. meningitidis* strain 247 X(Laboratory Center for Disease Control) wherein said strain was grown on a chemically defined medium (NCDM) for 18 hours. The said fermentation results in Men X polysaccharide yield of about 20 mg/L. Refer "Studies on the Group-specific Polysaccharide of *Neisseria meningitidis* Serogroup X and an improved Procedure for its isolation" JBC, 1974.

Ouli Xiea et al discloses preparation of MenX PS from strains BF7/07 and BF12/03. Briefly, the MenX strains were grown on Brain Heart Infusion agarplates with Levinthals' supplement, and following a pre-culturestep in 0.2 L Franz medium, the strain was cultivated in four separate 2.8 L baffled shaking flasks containing 1.0 or 1.5 L modified Franz liquid medium each. Liquid cultures were inactivated after 16 h of growth by adding formaldehyde to a final concentration of 1% (v/v). MenX PS yield per liter of growth medium appeared to be slightly higher for isolate BF 7/07 (4.5 mg/L) than for isolate BF12/03 (3.8 mg/L). Refer "Characterization of size, structure and purity of serogroup X *Neisseria meningitidis* polysaccharide, and development of an assay for quantification of human antibodies", Vaccine 30, 2012.

Prior art discusses structural and yield improvement studies with respect to polysaccharides from serogroups Men A, C, Y & W135. However none of the prior art addresses the long felt need for preparation of Men X polysaccharide with higher yield which is a prerequisite for development of Men X plain polysaccharide and Men X polysaccharide protein conjugate vaccines.

Present inventors have found that prior art feeding strategies based on pH stat, spiking and constant rate which are suitable for Men A C Y W135 fermentation, however suffer from following setbacks for Men X: i) satisfactory growth but less polysaccharide yield ii) growth limiting, less polysaccharide yield and iii) satisfactory growth but early decline phase. Further prior art methods employ soya peptone & yeast extract as feed medium components that result in lower polysaccharide yield associated with increased load of protein contaminants.

It is an object of the present invention to provide improved culture, fermentation and purification conditions for preparing *Neisseria meningitidis* X polysaccharides with high yield and minimum impurities With said improvements, Men X polysaccharide protein conjugate vaccine manufacturing can be economical and subsequently vaccine can be made available to children of developing countries at an affordable rate.

SUMMARY OF THE INVENTION

Present invention arises from the surprising finding that it is possible to prepare Men X polysaccharide with high yields and high purity by utilizing a) a fermentation medium containing casamino acid along with other components, b) novel continuous exponential feeding strategy and feed medium composition that can result in delaying the decline phase, c) optimal fermenter conditions and d) improved purification process devoid of chromatographic methods.

DETAILED DESCRIPTION OF INVENTION

Figure 1:
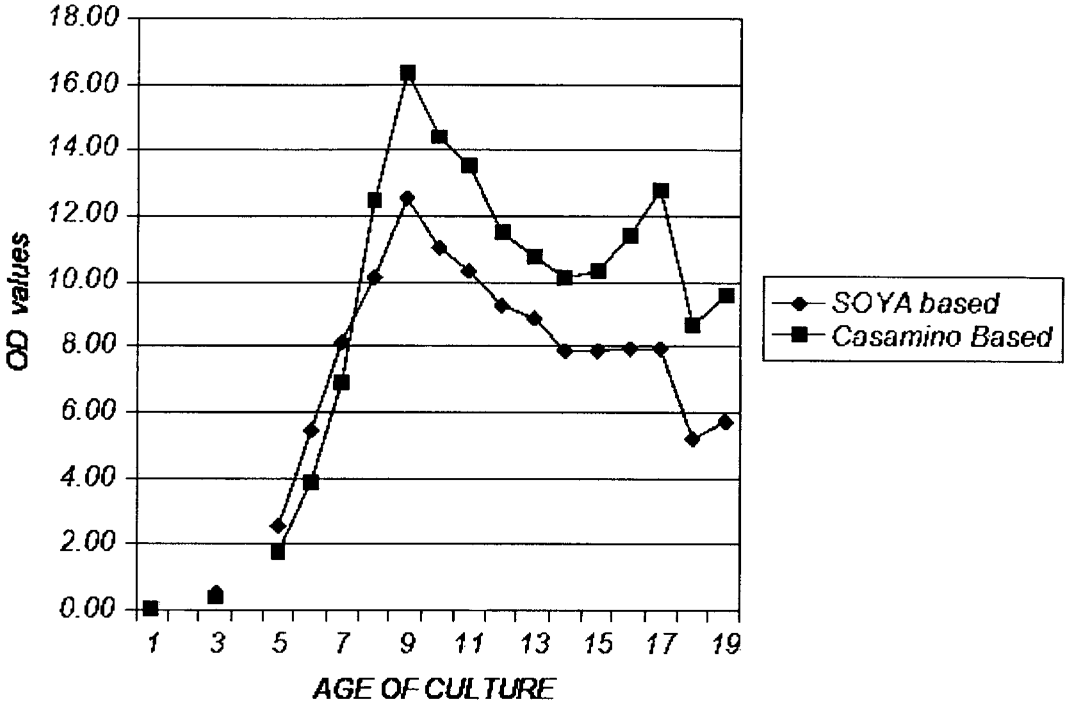
FIG. 1: Growth profile of "*N. meningitidis* X 821O" in medium containing casamino acid in comparison with medium containing soya peptone.
Figure 2:
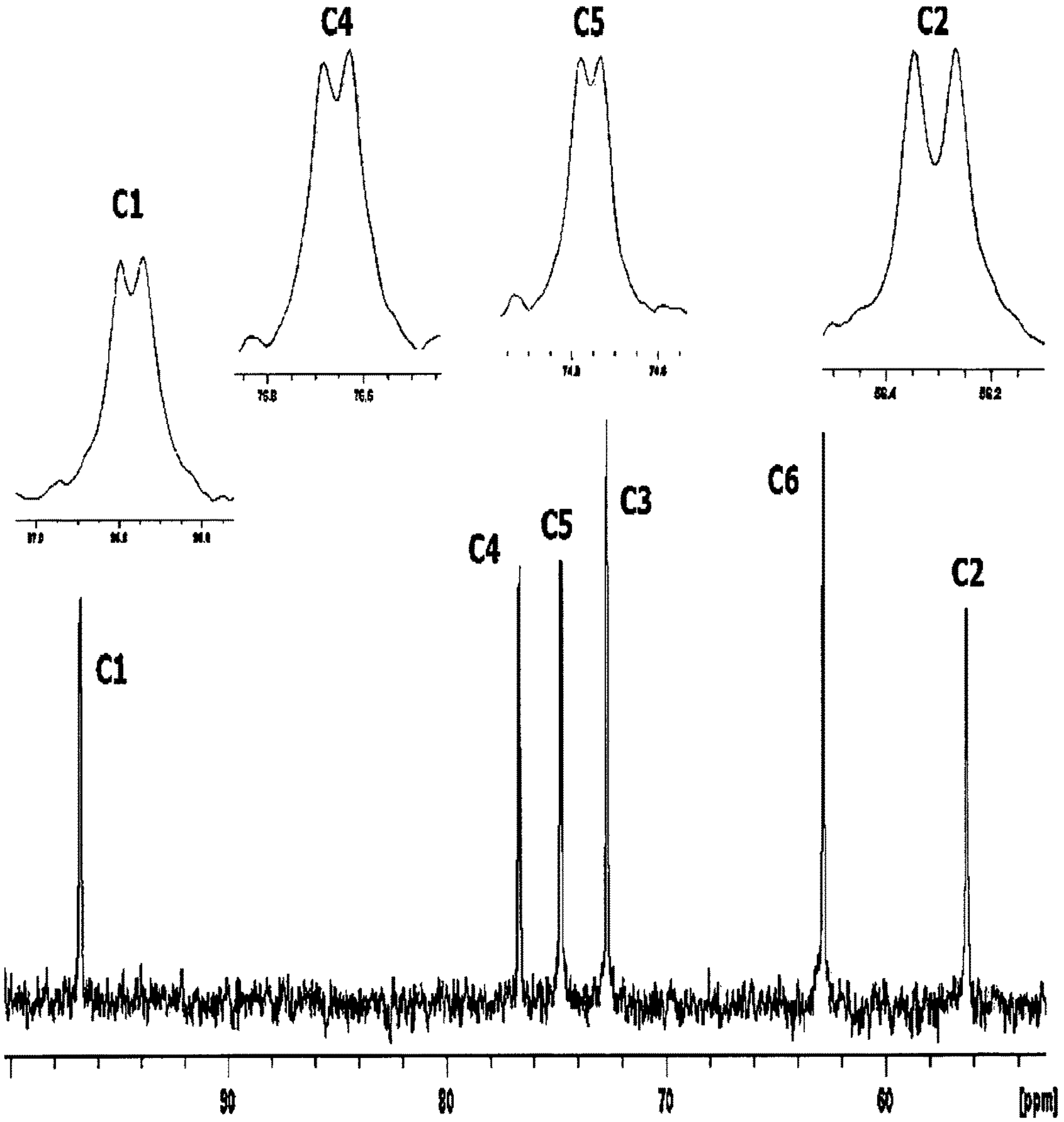
FIG. 2: $^{13}$C NMR Spectrum of Men X
Figure 3:
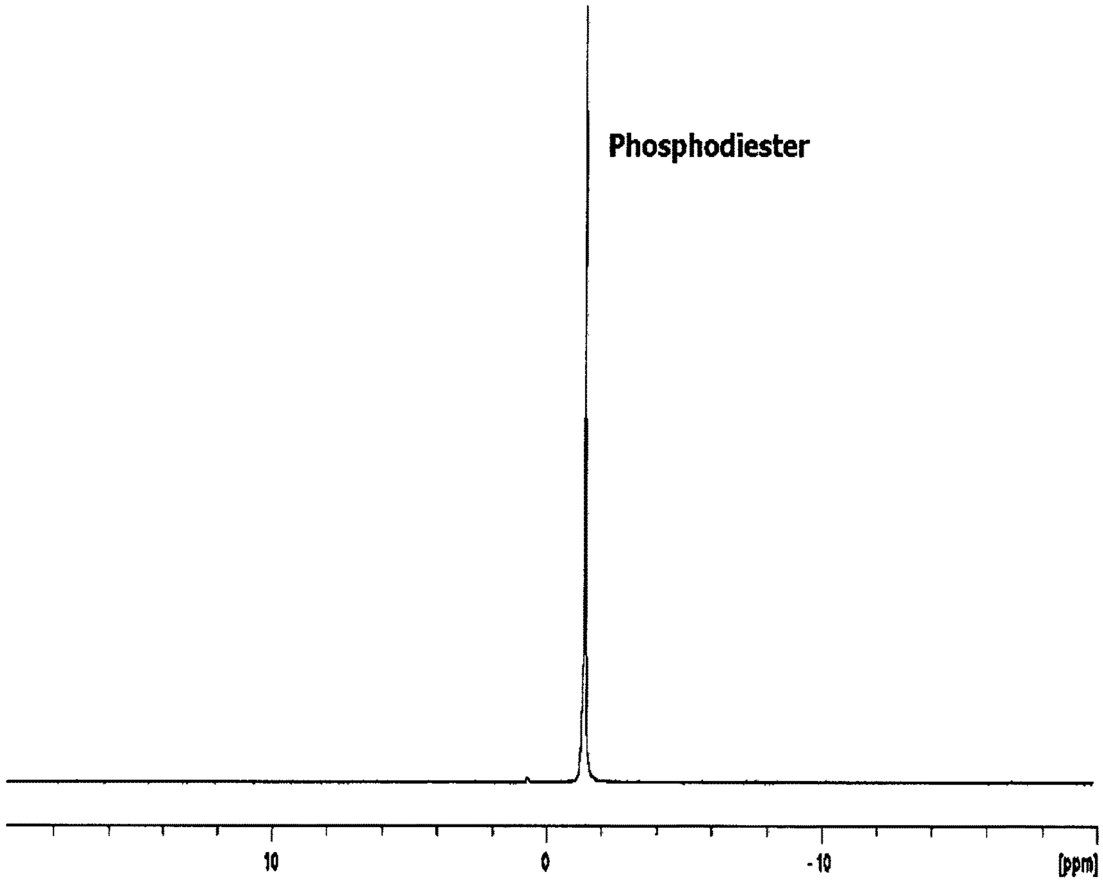
FIG. 3: $^{31}$P NMR Spectrum of Men X
Figure 4:
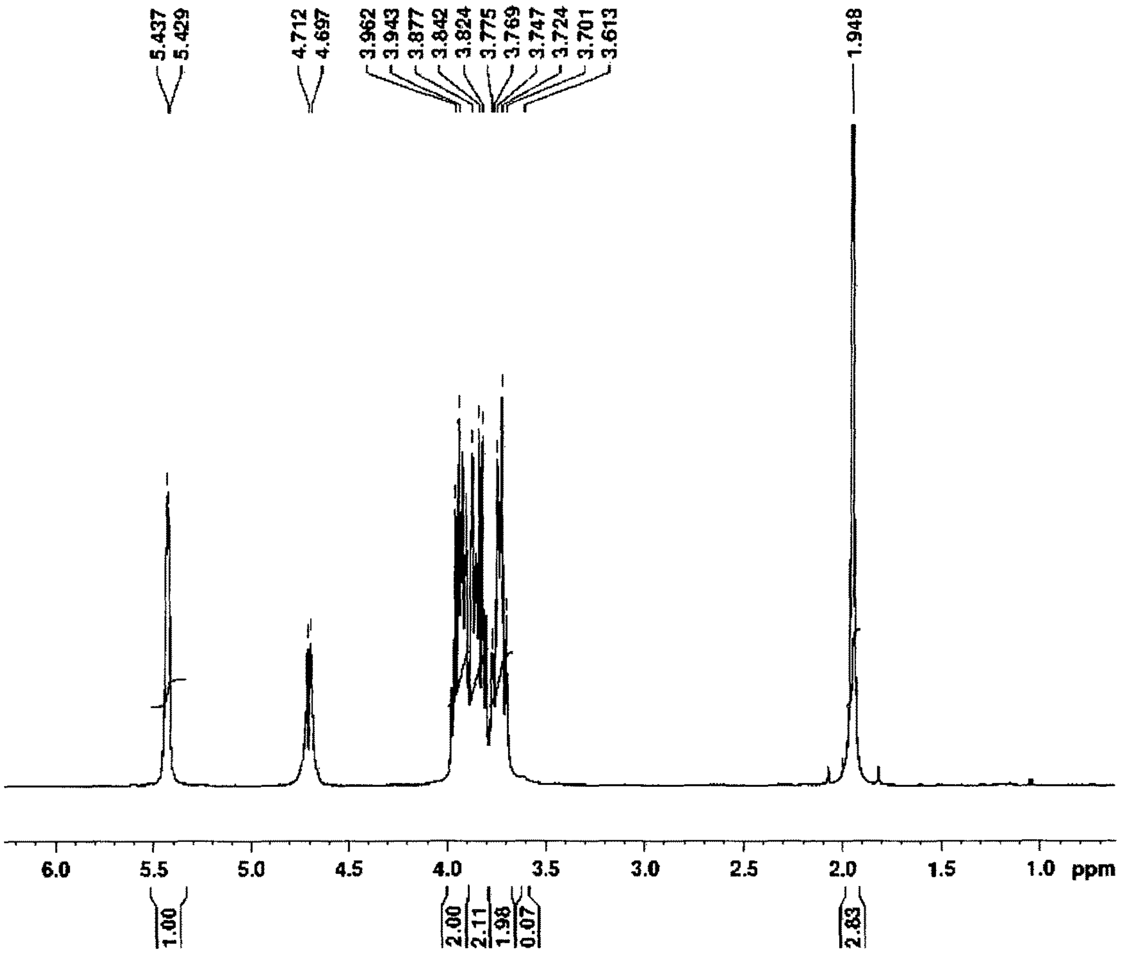
FIG. 4: $^{1}$H NMR Spectrum of Men X

Accordingly in a first embodiment, present invention preferably utilizes fermentation medium containing casamino acid as nitrogen source instead of soya peptone or yeast extract thereby providing following advantages i) significant increase in polysaccharide yield due to delay in decline phase as a result of utilization of a novel continuous exponential feeding strategy ii) 50% decrease in concentration of protein and nucleic acid contaminants at fermenter harvest 100 KDa stage itself, thereby ensuring that subsequent purification process can easily remove remaining impurities iii) scale up of fermentation medium containing casamino acid can be simple and economical.

A second embodiment of the instant invention is that said *Neisseria meningitidis* fermentation medium for producing capsular polysaccharides from *Neisseria meningitidis* X can comprise of dextrose between 9 and 10 g/l, sodium chloride between 5.5 and 6 g/l, potassium sulphate between 0.8 and 1 g/l, potassium phosphate dibasic between 3.5 and 4 g/l, ammonium chloride between 0.14 and 0.19 g/l, glutamic acid between 4.5 and 5.5 g/l, L-arginine between 0.2 and 0.4 g/l, L-serine between 0.4 and 0.6 g/l, L-cysteine between 0.24 and 0.26 g/l, magnesium chloride between 0.18 and 0.20, calcium chloride 0.02 g/l, ferrous sulphate 0.002 g/l & casamino acid between 5 and 20 g/l.

A preferred embodiment of the instant invention is that said *Neisseria meningitidis* fermentation medium for producing capsular polysaccharides from *Neisseria meningitidis* X can comprise of dextrose 10 g/l, sodium chloride between 5.8 and 6 g/l, potassium sulphate between 0.9 and 1 g/l, potassium phosphate dibasic between 3.8 and 4 g/l, ammonium chloride between 0.14 and 0.17 g/l, glutamic acid between 4.8 and 5 WI, L-arginine between 0.2 and 0.3 g/l, L-serine between 0.4 and 0.5 g/l, L-cysteine between 0.24 and 0.25 g/l, magnesium chloride between 0.18 and 0.19, calcium chloride 0.02 g/l, ferrous sulphate 0.002 g/l & casamino acid between 5 and 10 g/l.

An important aspect of the instant invention is that present inventors have surprisingly found an advantageous continuous exponential feeding strategy that can maintain cells in stationary phase for a longer duration, thereby increasing *N. meningitidis* X polysaccharide yield, such that the initial feed addition can be started when OD at 590 nm is between 3 to 4 at a rate of 10 ml/hr/1.5 L which gradually increases to 30 ml/hr/1.5 L till the culture OD is highest and then maintained at 60 ml/hr/1.5 L till culture OD reaches 50% of highest OD and then culture can be harvested.

Further inventors of present application have found that during fermentation to avoid pH drop resulting from accumulation of released cellular metabolites, NaoH at a concentration between 0.25N and 0.5N and orthophosphoric acid at a concentration between 5 and 10% can be continuously provided by the dosing pumps in cascade with the pH kept at set point, wherein ratio of sodium carbonate (20%) to NaoH (0.5N) is maintained at 1:3.

One important aspect of the instant invention is that said *N. meningitidis* X strain 8210 was found to have a log phase between 5$^{th}$ and 9$^{th}$ hr, stationary phase between 9$^{th}$ and 12$^{th}$ hr and decline phase between 12$^{th}$ and 19$^{th}$ hr.

The fermentation in the present invention may be carried out in batch or fed batch manner, preferably in a continuous fed batch mode.

In yet another aspect of the instant invention, said feed solution can comprise of dextrose between 72 and 76 g/l, sodium glutamate between 38 and 42 g/l, L-arginine between 2.8 and 3.2 g/l, L-serine between 2.8 and 3.2 g/l, L-cysteine between 1.9 and 2.1 g/l, magnesium chloride between 1.9 and 2.1, calcium chloride between 0.13 and 0.15 g/l and ferrous sulphate 0.02 g/l.

In a third embodiment, present invention provides a Men X capsular polysaccharide having yield between 600 mg/l to 800 mg/l at 100 KDa fermenter harvest stage wherein optical density measured at 590 nm can be between 8 and 15, preferably between 8 and 11.

A third embodiment of the present invention is that fermentation of *Neisseria meningitidis* X can be performed at set point values of i) pH from 7 to about 7.2, ii) temperature between 36 and 37° C. and at cascading values for i) dissolved oxygen from 15 to 25%, ii) agitation from 350-500 rpm, iii) Gas flow from 1 to 1.5, iv) Air from 0 to 100% and v) Oxygen from 0 to 100%.

A fourth embodiment of the instant invention is that the 100 KDa diafiltration harvest can be further subjected to purification steps comprising of:

(a) removal of protein and endotoxin impurities by utilizing deoxycholate at a concentration of 1% in combination with ethylenediaminetetraacetic acid at a concentration of 2 mM & ethanol at a concentration of 40%;

(b) addition of 4 to 6% sodium acetate for removal of nucleic acids;

(c) addition of cetyltrimethylammonium bromide at a concentration from 3 to 4% for binding polysaccharide and impurities;

(d) precipitation of polysaccharide from cetyltrimethylammonium, bromide-polysaccharide complex by utilizing sodium chloride at a concentration of 0.05 M in presence of 96% absolute ethanol;

(e) removal of protein and nucleic acid impurities by washing pellet with ethanol at a concentration of 45% in presence of sodium chloride at a concentration of 0.4 M;

(f) selective precipitation of polysaccharide by utilizing 96% absolute ethanol;

(g) dissolving polysaccharide in WFI and subjecting to tangential flow filtration; and wherein said purification process does not utilize any chromatography and said purified polysaccharide has yield from 300 to 500 mg/L, average molecular weight from 400 to 550 KDa, contains less than 0.5% proteins/peptides, less than 0.5% nucleic acids Jess than 5 EU/μg endotoxins with purification step recovery from 60% to 65%.

Another aspect of the fourth embodiment is that said *N. meningitidis* X polysaccharide purification process is robust and cost-efficient as it provides about 60 to 70% polysaccharide recovery and does not require any additional chromatographic steps.

A fifth aspect of the present invention is that said process can be applicable to *N. meningitidis* serotype X, A, B, C D, Y, Z, 29E and W-135, preferably to *N. meningitidis* serotype X strains selected from M9601, M9592, M9591, 247X, M9554, M8210 and M2526, 5967 strain (ST 750), most preferably to"M8210".

A sixth embodiment of the instant invention is that said *N. meningitidis* X polysaccharide of the instant invention can be utilized to prepare polysaccharide protein conjugate composition by methods disclosed in WO 201314268 wherein, i) polysaccharide X can be sized mechanically to obtain fragments having size between 150 and 200 KDa, ii) sized saccharide can be conjugated to carrier protein via a linker with a cyanylation conjugation chemistry iii) saccharide to protein ratio in final conjugate can be between 0.2-0.6.

In an aspect of sixth embodiment said *N. meningitidis* X polysaccharide of the instant invention can also be utilized to prepare a multivalent meningococcal polysaccharide protein conjugate composition comprising capsular saccharide from serogroups X and at least one additional capsular polysaccharide from A, C, W135 and Y by methods disclosed previously in WO 201314268.

Seventh embodiment of present invention is that said carrier protein can be selected from a group of but not limited to CRM 197, diphtheria toxoid, tetanus toxoid, pertussis toxoid, *E. coli* LT, *E. coli* ST, and exotoxin A from *Pseudomonas aeruginosa*, outer membrane complex c (OMPC), porins, transferrin binding proteins, pneumolysin, pneumococcal surface protein A (PspA), pneumococcal adhesin protein (PsaA), pneumococcal surface proteins BVH-3 and BVH-11, protective antigen (PA) of *Bacillus anthracis* and detoxified edema factor (EF) and lethal factor (LF) of *Bacillus anthracis*, ovalbumin, keyhole limpet hemocyanin (KLH), human serum albumin, bovine serum albumin (BSA) and purified protein derivative of tuberculin (PPD). Preferably, carrier proteins can be selected from tetanus toxoid, diphtheria toxoid and CRM197.

Monovalent or multivalent immunogenic compositions containing *N. meningitidis* X polysaccharide can be in a buffered liquid form or in a lyophilized form. Preferably, said polysaccharide protein conjugate can be lyophilized as disclosed previously in US2013/0209503, now U.S. Pat. No. 9,283,270 issued Mar. 15, 2016, wherein the formulation can have at least 6 months stability at 40° C. and free polysaccharide content can be less than 11% w/w.

The lyophilized vaccine composition of the present invention can be reconstituted with a delivery vehicle having pH from about 6 to 7.5, particularly with saline or PBS.

Compositions can comprise of aluminium salt adjuvant added at an amount of 25-125 μg of $Al^{+++}$ per 0.5 ml.

Also said composition can comprise of a preservative selected from thiomersal and 2-phenoxyethanol.

The lyophilized vaccine composition of the instant invention can be given as 1, 5 or 10 dose formulation.

The polysaccharide or a conjugate thereof is preferably administered parenterally, e.g. by injection or infusion by intravenous, intraperitoneal, intramuscular, intraarterial or intralesional route.

EXAMPLES

I) Fermentation Procedure:

Seed vial containing 3 ml of "*N. meningitidis* X M8210" (CBER) culture having OD 1/ml was freezed at −70° C. Then vial was thawed and seeded into 30 ml of seed medium which was incubated at 37° C. and agitated at 150 to 180 rpm. The volume was doubled to 60 ml when OD was above 0.7 and then to 120 ml, 210 ml respectively.

Culture having OD 10±0.2 with volume 70±10 ml was seeded into the reactor, wherein the medium volume in the reactor was 1500 ml. After inoculation of reactor 0 hr OD was maintained at 0.04 to 0.05.

The entire fermentation process was carried out in NBS bio flow Celligen 115 (2.2 L) glass bioreactor, wherein fermentation cycle was run in a continuous fed batch mode and total duration of fermentation cycle was 19 hrs.

II) Fermentation Medium Composition:

TABLE 1

Composition of novel medium containing casamino acid for *N. meningitidis* serogroup X(NMXM-CA-I)

| Component | Concentration (gm/l) |
|---|---|
| Dextrose | 10 |
| Sodium chloride | 5.8 |
| Potassium sulphate | 1 |
| Potassium phosphate dibasic | 4 |
| Ammonium chloride | 0.15 |

TABLE 1-continued

Composition of novel medium containing casamino acid for *N. meningitidis* serogroup X(NMXM-CA-I)

| Component | Concentration (gm/l) |
|---|---|
| Glutamic acid | 5 |
| Arginine | 0.3 |
| Serine | 0.5 |
| Cysteine | 0.25 |
| Magnesium chloride | 0.19 |
| Calcium chloride | 0.02 |
| Ferrous sulphate | 0.002 |
| Casamino acid | 10 |

TABLE 2

Composition of novel medium containing casamino acid for *N. meningitidis* serogroup X(NMXM-CA-II)

| Component | Concentration (gm/l) |
|---|---|
| Dextrose | 10 |
| Sodium chloride | 5.8 |
| Potassium sulphate | 1 |
| Potassium phosphate dibasic | 4 |
| Ammonium chloride | 0.15 |
| Glutamic acid | 5 |
| Arginine | 0.3 |
| Serine | 0.5 |
| Cysteine | 0.25 |
| Magnesium chloride | 0.19 |
| Calcium chloride | 0.02 |
| Ferrous sulphate | 0.002 |
| Casamino acid | 8 |

TABLE 3

Composition of novel medium containing casamino acid for *N. meningitidis* Serogroup X(NMXM-CA-III)

| Component | Concentration (gm/l) |
|---|---|
| Dextrose | 10 |
| Sodium chloride | 5.8 |
| Potassium sulphate | 1 |
| Potassium phosphate dibasic | 4 |
| Ammonium chloride | 0.15 |
| Glutamic acid | 5 |
| Arginine | 0.3 |
| Serine | 0.5 |
| Cysteine | 0.25 |
| Magnesium chloride | 0.19 |
| Calcium chloride | 0.02 |
| Ferrous sulphate | 0.002 |
| Casamino acid | 7 |

TABLE 4

Composition of a medium containing soya peptone for *N. meningitidis* serogroup X(NMXM-SP)

| Component | Concentration (gm/l) |
|---|---|
| Dextrose | 10 |
| Sodium chloride | 5.8 |
| Potassium sulphate | 1 |
| Potassium phosphate dibasic | 4 |
| Ammonium chloride | 0.15 |
| Glutamic acid | 5 |
| Arginine | 0.3 |
| Serine | 0.5 |
| Cysteine | 0.25 |
| Magnesium chloride | 0.19 |

TABLE 4-continued

Composition of a medium containing soya peptone for *N. meningitidis* serogroup X(NMXM-SP)

| Component | Concentration (gm/l) |
|---|---|
| Calcium chloride | 0.02 |
| Ferrous sulphate | 0.002 |
| Soya peptone | 9 |

TABLE 5

Composition of a medium containing soya peptone for *N. meningitidis* serogroup X(NMXM-SP-II)

| Component | Concentration (gm/l) |
|---|---|
| Dextrose | 10 |
| Sodium chloride | 5.8 |
| Potassium sulphate | 1 |
| Potassium phosphate dibasic | 4 |
| Ammonium chloride | 0.15 |
| Glutamic acid | 5 |
| Arginine | 0.3 |
| Serine | 0.5 |
| Cysteine | 0.25 |
| Magnesium chloride | 0.19 |
| Calcium chloride | 0.02 |
| Ferrous sulphate | 0.002 |
| Soya peptone | 8 |

III) Growth Kinetics, Novel Feeding Strategy & Feed Solutions:

TABLE 6

Growth profile of *N. meningitidis* X strain 8210

| Age | OD (590 nm) in medium containing casamino acid | OD (590 nm) in medium containing soya peptone |
|---|---|---|
| 0 | 0.07 | 0.08 |
| 1 | 0.19 | 0.23 |
| 2 | 0.40 | 0.55 |
| 3 | 0.80 | 1.27 |
| 4 | 1.73 | 2.55 |
| 5 | 3.89 | 5.49 |
| 6 | 6.93 | 8.17 |
| 7 | 12.45 | 10.08 |
| 8 | 16.40 | 12.49 |
| 9 | 14.40 | 11.03 |
| 10 | 13.49 | 10.33 |
| 11 | 11.48 | 9.28 |
| 12 | 10.74 | 8.84 |
| 13 | 10.09 | 7.89 |
| 14 | 10.29 | 7.92 |
| 15 | 10.32 | 7.97 |
| 16 | 11.32 | 7.94 |
| 17 | 11.67 | 5.21 |
| 18 | 11.54 | 5.77 |

The log phase was identified between $5^{th}$ and $9^{th}$ hr, stationary phase between $9^{th}$ and $12^{th}$ hr and decline phase between $12^{th}$ and $19^{th}$ hr.

Novel Feeding Strategy:

The feeding strategy was designed such that the initial feed addition can be started when OD at 590 nm is between 3 to 4 at a rate of 10 ml/hr/1.5 L which gradually increases to 30 ml/hr/1.5 L till the culture OD is highest and then maintained at 60 ml/hr/1.5 L till culture OD reaches 50% of highest OD and then culture can be harvested.

Feed Solutions:

TABLE 7

| Composition of novel "Feed Solution 1"(FS-1) for *N. meningitidis* serogroup X | |
|---|---|
| Component | Concentration (gm/l) |
| Dextrose | 75 |
| Sod glutamate | 40 |
| Arginine | 3 |
| Serine | 3 |
| Cysteine | 2 |
| Magnesium chloride | 2 |
| Calcium chloride | 0.15 |
| Ferrous sulphate | 0.02 |

TABLE 8

| Composition of novel "Feed Solution 2"(FS-2) for *N. meningitidis* serogroup X | |
|---|---|
| Component | Concentration (gm/l) |
| Dextrose | 75 |
| Sod glutamate | 40 |

Results:

Continuous exponential feeding strategy resulted in maintaining cells in stationary phase for a longer duration, thereby increasing yield of *N. meningitidis* X polysaccharide. Use of Casamino acid as a nitrogen source was found to provide high yield & high molecular weight Men X polysaccharide with minimal impurities at 100 Kda stage as compared to soya peptone as nitrogen source.

When only dextrose and sodium glutamate were used as feed solution (FS-2), cell morphology was affected ultimately resulting in unfavorable polysaccharide characteristics. Whereas when FS-1 (containing amino acids, salts in addition to dextrose and sodium glutamate) was used morphology of cells was found to be improved, thereby increasing polysaccharide yield and providing polysaccharide with favorable characteristics.

Study of growth profile of *N. meningitidis* X 8210 reveals that during fermentation a pH drop resulting from accumulation of released cellular metabolites was observed that was adversely affecting rate of capsular polysaccharide production. To avoid such pH drop, NaoH at a concentration between 0.25N and 0.5N and orthophosphoric acid at a concentration between 5 and 10% was continuously provided by the dosing pumps in cascade with the pH kept at set point, wherein ratio of sodium carbonate (20%) to NaoH (0.5N) is maintained at 1:3.

IV) Fermenter Conditions

TABLE 9

| Fermenter variables | |
|---|---|
| Fermentation aspect | Concentration |
| Temperature | 36° C. |
| OD | 16 OD |
| pH | 7.2 |
| DO (%) | 25% |
| Agitation (rpm) | 400 |

TABLE 9-continued

| Fermenter variables | |
|---|---|
| Fermentation aspect | Concentration |
| Gas flow | 1.0 |
| Air (%) | 0-100% |
| Oxygen (%) | 0-100% |

TABLE 10

| Polysaccharide Concentration & purity profile at 100 KDa | | |
|---|---|---|
| Nitrogen sources utilized | Polysaccharide concentration (mg/l) | Relative concentrations of Endotoxin, Protein & Nucleic acid |
| Men X Ps at 100 KDa fermentation harvest stage for NMXM-CA-I | 650 | Protein: 50-75%<br>Nucleic acid: 15-30% |
| Men X Ps at 100 KDa fermentation harvest stage for NMXM-CA-II | 625 | Protein: 42-70%<br>Nucleic acid: 15-30% |
| Men X Ps at 100 KDa fermentation harvest stage for NMXM-CA-III | 610 | Protein: 35-65%<br>Nucleic acid: 15-30% |
| Men X Ps at 100 KDa fermentation harvest stage for NMXM-SP-I | 500 | Protein: 65-95%<br>Nucleic acid: 15-40% |
| Men X Ps at 100 KDa fermentation harvest stage for NMXM-SP-II | 475 | Protein: 65-90%<br>Nucleic acid: 15-40% |

Results:

For NMXM-CA medium containing casamino acids, at 100 KDa stage, polysaccharide yield was between 500 and 650 mg/1 with minimal load of wherein harvesting was carried at when OD reached 50% of highest culture OD. Whereas for NMXM-SP medium containing soya peptone, at 100 KDa stage, polysaccharide yield was comparatively low i.e. between 450 and 500 mg/1 with greater load of impurities.

V) Harvesting & Inactivation

The fermentation was terminated once drop in optical density was observed followed by inactivation using 1% formaldehyde for 2 hrs at 37° C. Further the temperature was reduced at 10° C. and incubated for 30 minutes. The harvest was unloaded and centrifuged at 14,500 g for 45 minutes.

Then supernatant was subjected to 0.2μ filtration followed by 100 KD diafiltration (10-15 times) and was further concentrated with WFI. Later sterile filtration with 0.2μ filter was carried.

VI) Purification of Men X Polysaccharide

Protocol 1:

Addition of 0.5% deoxycholate, 6% sodium acetate, 2 mM EDTA & 40% ethanol to the 100 KD diafiltered harvest. Then the mixture was kept at 2-8° C. for 3-4 hrs with stirring. Later mixture was subjected to centrifugation at 10000 rpm for 20 min and supernatant was diafiltered against 25 mM Tris with 100 KD cassette membrane. Further 10% w/v CTAB precipitation was carried overnight at 2-8° C. with stirring and pellet was collected. Said pellet was dissolved in 96% ethanol with 0.05M NaCl at 2-8° C. for 2 hrs on stirring. Then polysaccharide precipitation was carried for 30 minutes and pellet was collected. Said pellet was dissolved in 45% ethanol with 0.4M NaCl for 1 hr. The supernatant was collected & filtered through CUNO R32SP carbon filter. Then polysaccharide was precipitated in 96% ethanol for 1-2 his and pellet was collected. Then pellet was dissolved in WFI followed by TFF. Final purified *N. meningitidis* X polysaccharide was stored at −20° C.

Protocol 2:

Addition of 1.5% deoxycholate, 6% sodium acetate, 2 mM EDTA & 40% ethanol to the 100 KD diafiltered harvest. Then the mixture was kept at 2-8° C. for 3-4 hrs with stirring. Later mixture was subjected to centrifugation at 10000 rpm for 20 min and supernatant was diafiltered against 25 mM Tris with 100 KD cassette membrane. Further 6% w/v CTAB precipitation was carried overnight at 2-8° C. with stirring and pellet was collected. Said pellet was dissolved in 96% ethanol with 0.05M NaCl at 2-8° C. for 2 hrs on stirring. Then polysaccharide precipitation was carried for 30 minutes and pellet was collected. Said pellet was dissolved in 45% ethanol with 0.4M NaCl for 1 hr. The supernatant was collected & filtered through CUNO R32SP carbon filter. Then polysaccharide was precipitated in 96% ethanol for 1-2 hrs and pellet was collected. Then pellet was dissolved in WFI followed by TFF. Final purified *N. meningitidis* X polysaccharide was stored at −20° C.

Protocol 3:

Addition of 1% deoxycholate, 6% sodium acetate, 2 mM EDTA & 40% ethanol to the 100 KD diafiltered harvest. Then the mixture was kept at 2-8° C. for 3-4 hrs with stirring. Later mixture was subjected to centrifugation at 10000 rpm for 20 min and supernatant was diafiltered against 25 mM Tris with 100 KD cassette membrane. Further 3% w/v CTAB precipitation was carried overnight at 2-8° C. with stirring and pellet was collected. Said pellet was dissolved in 96% ethanol with 0.05M NaCl at 2-8° C. for 2 hrs on stirring. Then polysaccharide precipitation was carried for 30 minutes and pellet was collected. Said pellet was dissolved in 45% ethanol with 0.4M NaCl for 1 hr. The supernatant was collected & filtered through CUNO R32SP carbon filter. Then polysaccharide was precipitated in 96% ethanol for 1-2 hrs and pellet was collected. Then pellet was dissolved in WFI followed by TFF. Final purified *N. meningitidis* X polysaccharide was stored at −20° C.

Protocol 1 having low DOC resulted caused inefficient removal of contaminants (protein/nucleic acids) whereas & high CTAB concentrations resulted in a complex of CTAB-polysaccharide that was not readily separable.

Protocol 2 having higher DOC resulted in more viscous polysaccharide solutions thus making it difficult for TFF processing. Also intermediate CTAB concentration resulted in a complex of CTAB-polysaccharide that was not readily separable.

Protocol 3 having intermediate DOC and less CTAB concentration was found to be more efficient than Protocol 1/2 and hence was finalized for purification of *N. meningitidis* X polysaccharide.

The purified *N. meningitidis* X polysaccharide prepared by Protocol 3 was tested for impurities like Protein, Nucleic acid, Endotoxin and Molecular size. Although WHO specification/guidelines for Men X polysaccharide were not available, purified *N. meningitidis* X polysaccharide was found to meet WHO specifications already set for a similar phosphodiester containing polysaccharide i.e. *N. meningitidis* A.

Further, comparison of $^{1}H$, $^{13}C$, $^{31}P$ NMR assignments of SIIL's Men X polysaccharide with recently published X-related NMR data (Vaccine 30, 2012, 5812-5823 & Vaccine 30, 2012, 6409-6415) confirm structural identity of SIIL's Men X polysaccharide.

TABLE 11

Characteristics of Purified Men X polysaccharide

| Nitrogen sources utilized | Ps Conc (mg/l) | Nucleic acid (%) | Endotoxin (Eu/ug) | Protein (%) | Mw (KDa) |
|---|---|---|---|---|---|
| Men X Ps for NMXM-CA-I | 440 | 0.062 | 1.51 | 0.18 | 410 |
| Men X Ps for NMXM-CA-II | 420 | 0.047 | 1.33 | 0.14 | 520 |
| Men X Ps for NMXM-CA-III | 380 | 0.052 | 1.25 | 0.13 | 549 |
| Men X Ps for NMXM-SP-I | 300 | 0.081 | 1.90 | 0.19 | 380 |
| Men X Ps for NMXM-SP-II | 250 | 0.062 | 1.25 | 0.15 | 463 |

Results:

Both, NMXM-CA NMXM-SP based batches of Men. X polysaccharide were found to meet WHO specifications set for *N. meningitidis* A polysaccharide.

For NMXM-CA medium containing casamino acids, at final purified stage, purification step recovery was between 60 and 65%, polysaccharide yield was between 350 and 500 mg/l with minimal load of impurities when harvesting was carried when culture OD reaches 50% of highest culture OD. Whereas for NMXM-SP medium containing soya peptone, at final purified stage, purification step recovery for polysaccharide as well as polysaccharide yield was comparatively low along with greater load of impurities.

Above high Men X polysaccharide yield was achieved without utilizing any additional chromatographic methods, thereby demonstrating that above purification protocol is robust & cost-efficient.

VII) Preparation of Lyophilized, Immunogenic MenX Polysaccharide-Protein Conjugates:

Monovalent or multivalent immunogenic compositions containing *N. meningitidis* X polysaccharide-tetanus toxoid can be in a buffered liquid form or in a lyophilized form.

Preferably, said polysaccharide protein conjugate can be lyophilized as disclosed previously in US 2013/0209503, now U.S. Pat. No. 9,283,270 which issued Mar. 15, 2006, wherein the formulation can have at least 6 months stability at 40° C. and free polysaccharide content can be less than 11% w/w.

Men X polysaccharide of the instant invention can be utilized to prepare immunogenic, multivalent meningococcal polysaccharide protein conjugate compositions comprising capsular saccharide from serogroups X and at least one capsular saccharide from A, C, W135 and Y as discussed previously in WO 201314268.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims, We therefore claim as our invention all that comes within the scope and spirit of these claims.

We claim:

1. A method for preparing a capsular polysaccharide of *Neisseria meningitidis* X with high yield and high purity, comprising the steps of:

(a) preparing an aqueous fermenter nutrient medium comprising casamino acid;

(b) inoculating the fermenter nutrient medium with a *Neisseria meningitidis* X bacterium having optical density at 590 nm of 0.8 to 1.2;

(c) continuous exponential feeding with a feed solution with a feed addition rate varying between 10 mL/hr/1.5 L and 60 mL/hr/1.5 L beginning at an OD at 590 nm between 3 and 4;

(d) incubating the inoculated fermenter nutrient medium under controlled conditions of pH, temperature and dissolved oxygen percentage;

(e) harvesting the capsular polysaccharide produced in step (d) when the optical density (OD) at 590 nm is less than 60% of the highest culture OD at 590 nm;

(f) purifying the capsular saccharide obtained in step (e);

(g) optionally concentrating the purified capsular polysaccharide obtained in step (f); and wherein said purified polysaccharide has yield from 300 to 550 mg/L, average molecular weight from 400 to 550 KDa, purification step recovery from 60% to 65% and contains less than 0.5% proteins/peptides, less than 0.5% nucleic acids and less than 5 EU/μg endotoxins.

2. A process for the production of *Neisseria meningitides* capsular polysaccharide as claimed in claim 1 wherein:

(a) said capsular polysaccharide producing bacteria is selected from *N. meningitidis* X strains M8210, M9601, M9591, M9592, M9554, M2526, 247X and 5967(ST 750);

(b) said fermenter nutrient medium comprises:

(i) casamino acids at an amount 5 g/L to 20 g/L, 0.14 g/L to 0.19 g/L Ammonium chloride, 10 g/L to 11 g/L dextrose, 5.8 g/L to 6 g/L Sodium chloride, 0.9 g/L to 1 g/L Potassium sulphate, 3.8 g/L to 4 g/L Potassium phosphate dibasic, 4.8 g/L to 5 g/L Glutamic acid, 0.2 g/L to 0.3 g/L L-Arginine, 0.4 g/L to 0.5 g/L L-Serine, 0.24 g/L to 0.25 g/L L-Cysteine, 0.18 g/L to 0.19 g/L Magnesium chloride, 0.02 g/L Calcium chloride and 0.002 g/L Ferrous sulphate such that concentration of components of the medium may vary by ±10%; or (ii) casamino acids at an amount 5 g/L to 10 g/L, 0.14 g/L to 0.17 g/L Ammonium chloride, 10 g/L to 11 g/L dextrose, 5.8 g/L to 6 g/L Sodium chloride, 0.9 g/L to 1 g/L Potassium sulphate, 3.8 g/L to 4 g/L Potassium phosphate dibasic, 4.8 g/L to 5 g/L Glutamic acid, 0.2 g/L to 0.3 g/L L-Arginine, 0.4 g/L to 0.5 g/L L-Serine, 0.24 g/L to 0.25 g/L L-Cysteine, 0.18 g/L to 0.19 g/L Magnesium chloride, 0.02 g/L Calcium chloride and 0.002 g/L Ferrous sulphate such that concentration of components of the medium may vary by ±10%;

(c) said inoculation of fermenter nutrient medium is by a seed inoculum having an optical density of 0.8 to 1;

(d) said continuous exponential feeding begins with initial feed addition at a rate of 10 mL/hr/1.5 L when OD at 590 nm is between 3 to 4 which gradually increases to 30 mL/hr/1.5 L until the culture OD at 590 nm is highest and then maintained at 60 mL/hr/1.5 L until culture OD at 590 nm reaches 50% of highest OD at 590 nm when culture can be harvested;

(e) said feed solution comprises of 72 to 76 g/L dextrose, 38 g/L to 42 g/L Sodium glutamate, 2.8 g/L to 3.2 g/L L-Arginine, 2.8 g/L to 3.2 g/L L-Serine, 1.9 g/L to 2.1 g/L L-Cysteine, 1.9 g/L to 2 g/L Magnesium chloride, 0.13 g/L to 0.15 g/L Calcium chloride and 0.02 g/L Ferrous sulphate such that concentration of components of the feed solution may vary by ±10%;

(f) said incubation is carried out (i) at a temperature of 36° C. to 37° C., at a pH of 7-7.2, at 350 to 500 rpm, dissolved oxygen percentage of 15% to 25%, Gas flow at 1 to 1.5, Air at 0 to 100% and Oxygen at 0 to 100% for 7 to 10 hours or (ii) at a temperature of 36° C., at a pH 7.2, at about 400 rpm, dissolved oxygen percentage of 25%, Gas flow at 1 to 1.5;

(iii) Air at 0 to 100% and Oxygen at 0 to 100% for 8 to 9 hours;

(g) said inactivation is carried out using 1% formaldehyde for 1 to 2 hrs at 37° C. followed by incubation at 10° C. for 30 minutes;

(i) said harvesting is carried out by (i) centrifugation at 14500 g for 45 minutes to remove all cell residues to obtain a supernatant;

(ii) subjecting the supernatant to 0.2μ filtration followed by 100 KD diafiltration and concentration with water for injection (WFI);

and (h) said process is carried out in continuous fed-batch culture system.

3. The process of claim 1 wherein step (f) comprises:

(a) removal of protein and endotoxin impurities by utilizing anionic detergent at a concentration from 1 to 1.2% in combination with a chelating agent at a concentration from 1.5 to 3 mM and alcohol at a concentration from 40% to 50%;

(b) addition of sodium acetate at a concentration from 4 to 6% for removal of nucleic acids;

(c) addition of a cationic detergent at 3 to 4% for binding polysaccharides and impurities;

(d) precipitation of polysaccharides from cationic detergent-polysaccharide complex by utilizing sodium chloride at 0.05 M in presence of 96% alcohol;

(e) removal of protein and nucleic acid impurities by washing the precipitated polysaccharides with 45% alcohol in the presence of sodium chloride at a concentration of 0.4 M;

(f) selective precipitation of polysaccharides by utilizing 96% alcohol;

(g) dissolving the precipitated polysaccharides in WFI and subjecting the dissolved polysaccharides to tangential flow filtration;

and wherein said purification process does not utilize any chromatography.

4. The process of claim 3, wherein purification comprises the following steps:

(a) removal of protein and endotoxin impurities by utilizing deoxycholate at a concentration of 1% in combination with ethylenediaminetetraacetic acid at a concentration of 2 mM and ethanol at a concentration of 40%;

(b) addition of 4 to 6% sodium acetate for removal of nucleic acids;

(c) addition of cetyltrimethylammonium bromide at a concentration from 3 to 4% for binding polysaccharides and impurities;

(d) precipitation of polysaccharides from the cetyltrimethylammonium bromide-polysaccharide complex by utilizing sodium chloride at a concentration of 0.05 M in presence of 96% ethanol;

(e) removal of protein and nucleic acid impurities by washing the precipitated polysaccharides with ethanol at a concentration of 45% in the presence of sodium chloride at a concentration of 0.4 M;

(f) selective precipitation of polysaccharides by utilizing 96% ethanol;

(g) dissolving the precipitated polysaccharides in WFI and subjecting the dissolved polysaccharides to tangential flow filtration;

and wherein said purification process does not utilize any chromatography.

5. The method according to claim 1, further comprising step (h) wherein purified *N. meningitidis* X polysaccharide is sized to an average size of between 100 and 150 Kda by using high pressure cell disruption system.

6. The method according to claim 5, further comprising the step of conjugating said size reduced polysaccharide to a carrier protein, to yield a protein-polysaccharide conjugate and formulating an immunogenic composition comprising said protein-polysaccharide conjugate.

7. The method according to claim 6, wherein said *N.meningitidis* X polysaccharide is conjugated to a carrier protein selected from the group consisting of Tetanus toxoid (TT), Diphtheria toxoid (DT), Cross Reaching Material (Mutant Diphtheria toxoid) (CRM197), fragment C of TT, protein D, Outer Membrane Protein Complex (OMPC) and pneumolysin.

8. The method according to claim 6, wherein said *N. meningitidis* X polysaccharide is conjugated to the carrier protein via a hetero or homo-bifunctional linker by cyanylation.

9. The method according to claim 8, wherein said cyanylation reagent is selected from a group of 1-cyano-4-pyrrolidinopyridinium tetrafluoroborate (CPPT), 1-cyano-imidazole (1-CI), 1-cyanobenzotriazole (1-CBT), or 2-cyanopyridazine-3(2H) one (2-CPO), or a functional derivative or modification thereof.

10. An immunogenic composition prepared according to claim 6, wherein further the protein-polysaccharide conjugates are in a lyophilized form.

11. An immunogenic composition prepared according to claim 6, wherein further the protein-polysaccharide conjugates are in a buffered liquid form.

12. An immunogenic composition prepared according to claim 6, wherein further one or more *N.meningitidis* protein-polysaccharide conjugates are optionally adsorbed onto aluminium hydroxide, aluminium phosphate or a mixture of both or unadsorbed onto an adjuvant.

13. An immunogenic composition according to claim 12, further comprising an aluminium salt adjuvant at an amount of 25-125 μg of $Al^{+++}$ per 0.5 mL.

14. An immunogenic composition according to claim 13, further comprising a preservative selected from thiomersal and 2-phenoxyethanol.

15. An immunogenic lyophilized monovalent or multivalent vaccine composition containing a *N. meningitidis* serogroup X polysaccharide-protein conjugate prepared according to claim 10 wherein said vaccine is given as a 1, 5 or 10 dose formulation.

16. A method for preparing a *N. meningitidis* serogroup X capsular polysaccharide with high yields and high purity which comprises the steps of:

(i) preparing a fermentation medium composition containing casamino acids and ammonium chloride and inoculating the composition with a *Neisseria meningitides* serogroup X bacterium composition having an optical density at 590 nm of 0.8 to 1.2;

(ii) continuous exponential feeding with a feed solution with a feed addition rate varying between 10 mL/hr/1.5 L and 60 mL/hr/1.5 L beginning at an OD at 590 nm between 3 and 4;

(iii) incubating the inoculated fermenter nutrient medium under controlled conditions of pH, temperature and dissolved oxygen percentage;

(iv) harvesting the capsular polysaccharide produced in step (iii) when the optical density (OD) at 590 nm is less than 60% of the highest culture OD at 590 nm; and (v) recovering and purifying the *Neisseria meningitidis* serogroup X capsular polysaccharide obtained in (iv);

and wherein said purified *Neisseria meningitidis* serogroup X polysaccharide yields from 300 to 550 mg/L, has an average molecular weight from 400 to 550 KDa, contains less than 0.5% proteins/peptides, less than 0.5% nucleic acids, less than 5 EU/μg endotoxins and said purification step recovery is from 60% to 65%.

17. A method for preparing a *Neisseria meningitides* serogroup X capsular polysaccharide with high yields and high purity which comprises the steps of:

i) preparing a fermentation medium composition comprising a combination of casamino acid and at least one additional nitrogen source selected from soya peptone and yeast extract and inoculating the composition with a *Neisseria meningitidis* X bacterium composition having an optical density at 590 nm of 0.8 to 1.2;

(ii) continuous exponential feeding with a feed solution with a feed addition rate varying between 10 mL/hr/1.5 L and 60 mL/hr/1.5 L beginning at an OD at 590 nm between 3 and 4 at 590 nm;

(iii) incubating the inoculated fermenter nutrient medium under controlled conditions of pH, temperature and dissolved oxygen percentage;

(iv) harvesting the capsular polysaccharide produced in step (iii) when the optical density (OD) at 590 nm is less than 60% of the highest culture OD at 590 nm; and (v) recovering and purifying the *Neisseria meningitidis* X capsular polysaccharide obtained in (iv) without using chromatography;

and wherein said purification purified *Neisseria meningitidis* X polysaccharide has yields from 300 to 550 mg/L, has an average molecular weight from 400 to 550 KDa, contains less than 0.5% proteins/peptides, less than 0.5% nucleic acids, less than 5 EU/μg endotoxins and said purification step recovery is from 60% to 65%.

18. A method for preparing a *Neisseria meningitides* serogroup X capsular polysaccharide with high yields and high purity which comprises the steps of:

i) providing a fermentation medium composition comprising a combination of casamino acid, ammonium chloride and at least one additional nitrogen source selected from soya peptone and yeast extract and inoculating the composition with a *Neisseria meningitidis* X bacterium composition having an optical density at 590 nm of 0.8 to 1.2;

(ii) continuous exponential feeding with a feed solution with a feed addition rate varying between 10 mL/hr/1.5 L and 60 mL/hr/1.5 L beginning at an OD at 590 nm between 3 and 4;

(iii) incubating the inoculated fermenter nutrient medium under controlled conditions of pH, temperature and dissolved oxygen percentage;

(iv) harvesting the capsular polysaccharide produced in step (iii) when the optical density (OD) at 590 nm is less than 60% of the highest culture OD at 590 nm; and (v) recovering and purifying the *Neisseria meningitidis* X capsular polysaccharide obtained in (iv) without using chromatography;

wherein said purification purified *Neisseria meningitidis* X polysaccharide yields from 300 to 550 mg/L, has an average molecular weight from 400 to 550 KDa, contains less than 0.5% proteins/peptides, less than 0.5% nucleic acids, less than 5 EU/μg endotoxins and said purification step recovery is from 60% to 65%.

* * * * *